United States Patent
Pavlov et al.

(10) Patent No.: US 7,608,105 B2
(45) Date of Patent: *Oct. 27, 2009

(54) METHODS OF INSERTING CONICALLY-SHAPED FUSION CAGES

(75) Inventors: Paul W. Pavlov, Nijmegen (NL); Charles J. Winslow, Walnut Creek, CA (US); Kirk Jayne, Alameda, CA (US); Henry A. Klyce, Piedmont, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 464 days.

This patent is subject to a terminal disclaimer.

(21) Appl. No.: 11/185,418

(22) Filed: Jul. 20, 2005

(65) Prior Publication Data
US 2005/0256575 A1 Nov. 17, 2005

Related U.S. Application Data

(63) Continuation of application No. 10/350,834, filed on Jan. 24, 2003, now abandoned, which is a continuation of application No. 09/358,188, filed on Jul. 20, 1999, now abandoned, which is a continuation of application No. 08/781,525, filed on Jan. 9, 1997, now abandoned, which is a continuation of application No. 08/306,879, filed on Sep. 15, 1994, now abandoned.

(51) Int. Cl.
*A61F 2/44* (2006.01)
(52) U.S. Cl. .................. 623/17.11; 623/17.16
(58) Field of Classification Search ... 623/17.11–17.16; 606/61, 247, 279
See application file for complete search history.

(56) References Cited

U.S. PATENT DOCUMENTS 2,537,070 A 1/1951 Longfellow
3,112,743 A 12/1963 Cochran et al.
3,298,372 A 1/1967 Feinberg
3,426,364 A 2/1969 Lumb
3,465,398 A 9/1969 Rector (Continued)

FOREIGN PATENT DOCUMENTS

DE 3505567 A1 6/1986

(Continued)

OTHER PUBLICATIONS

"Basket Implant Facilitates Spinal Fusion", Orthopedics Today, vol. 7, No. 10, Oct. 1987, p. 4.

(Continued)

*Primary Examiner*—Pedro Philogene
(74) *Attorney, Agent, or Firm*—Lerner, David, Littenberg, Krumholz & Mentlik, LLP

(57) ABSTRACT

A method of promoting fusion of adjacent vertebral bodies include providing a conically-shaped cage body having bone engaging projections on an outer surface thereof, the cage body including a leading end having a first diameter and a trailing end having a second diameter that is larger than the first diameter. The method also includes positioning the leading end of the cage body adjacent an intervertebral disc space between an upper vertebral body and a lower vertebral body, whereby the upper and lower vertebral bodies have opposing end faces that define upper and lower limits of the intervertebral disc space. While urging the leading end of the cage body into the intervertebral disc space, the cage body is turned so that the bone engaging projections bite into the opposing end faces of the upper and lower vertebral bodies for anchoring the cage body to the upper and lower vertebral bodies.

26 Claims, 8 Drawing Sheets

U.S. PATENT DOCUMENTS

| | | | |
|---|---|---|---|
| 3,486,505 A | 12/1969 | Morrison | |
| 3,514,791 A | 6/1970 | Sparks | |
| 3,625,198 A | 12/1971 | Sparks | |
| 3,719,186 A | 3/1973 | Merig, Jr. | |
| 3,720,959 A | 3/1973 | Hahn | |
| 3,783,860 A | 1/1974 | Burstein et al. | |
| 3,848,601 A | 11/1974 | Ma et al. | |
| 3,849,805 A | 11/1974 | Leake et al. | |
| 3,852,045 A | 12/1974 | Wheeler et al. | |
| 3,855,638 A | 12/1974 | Pilliar | |
| 3,867,728 A | 2/1975 | Stubstad et al. | |
| 3,871,031 A | 3/1975 | Boutin | |
| 3,905,047 A | 9/1975 | Long | |
| 3,906,550 A | 9/1975 | Rostoker et al. | |
| 3,916,907 A | 11/1975 | Peterson | |
| 3,986,212 A | 10/1976 | Sauer | |
| 4,013,071 A | 3/1977 | Rosenberg | |
| 4,016,651 A | 4/1977 | Kawahara et al. | |
| 4,059,115 A | 11/1977 | Jumashev et al. | |
| 4,086,701 A | 5/1978 | Kawahara et al. | |
| 4,124,026 A | 11/1978 | Berner et al. | |
| 4,177,524 A | 12/1979 | Grell et al. | |
| 4,180,910 A | 1/1980 | Straumann et al. | |
| 4,185,383 A | 1/1980 | Heimke et al. | |
| 4,259,072 A | 3/1981 | Hirabayashi et al. | |
| 4,289,123 A | 9/1981 | Dunn | |
| 4,309,777 A | 1/1982 | Patil | |
| 4,328,593 A | 5/1982 | Sutter et al. | |
| 4,349,921 A | 9/1982 | Kuntz | |
| 4,401,112 A | 8/1983 | Rezaian | |
| 4,406,623 A | 9/1983 | Grafellmann et al. | |
| RE31,628 E | 7/1984 | Allgower et al. | |
| 4,468,200 A | 8/1984 | Munch | |
| 4,484,570 A | 11/1984 | Sutter et al. | |
| 4,492,226 A | 1/1985 | Belykh et al. | |
| 4,493,317 A | 1/1985 | Klaue | |
| 4,501,269 A | 2/1985 | Bagby | |
| RE31,865 E | 4/1985 | Roux | |
| 4,511,336 A | 4/1985 | Hidaka et al. | |
| 4,513,744 A | 4/1985 | Klaue | |
| 4,522,200 A | 6/1985 | Stednitz | |
| 4,525,145 A | 6/1985 | Scheicher et al. | |
| 4,537,185 A | 8/1985 | Stednitz | |
| 4,545,374 A | 10/1985 | Jacobson | |
| 4,549,319 A | 10/1985 | Meyer | |
| 4,553,273 A | 11/1985 | Wu | |
| 4,569,338 A | 2/1986 | Edwards | |
| 4,573,448 A | 3/1986 | Kambin | |
| 4,599,084 A | 7/1986 | Nashef | |
| 4,599,086 A | 7/1986 | Doty | |
| 4,611,581 A | 9/1986 | Steffee | |
| 4,636,217 A | 1/1987 | Ogilvie et al. | |
| 4,653,481 A | 3/1987 | Howland | |
| 4,653,486 A | 3/1987 | Coker | |
| 4,655,199 A | 4/1987 | Steffee | |
| 4,657,550 A | 4/1987 | Daher | |
| 4,662,891 A | 5/1987 | Noiles | |
| 4,673,409 A | 6/1987 | Van Kampen | |
| 4,677,972 A | 7/1987 | Tornier | |
| 4,714,469 A | 12/1987 | Kenna | |
| 4,721,103 A | 1/1988 | Freedland | |
| 4,725,280 A | 2/1988 | Laure | |
| 4,736,738 A | 4/1988 | Lipovsek | |
| 4,743,256 A | 5/1988 | Brantigan | |
| 4,743,260 A | 5/1988 | Burton | |
| 4,759,768 A | 7/1988 | Hermann et al. | |
| 4,769,041 A | 9/1988 | Morscher | |
| 4,772,287 A | 9/1988 | Ray | |
| 4,790,297 A | 12/1988 | Luque | |
| 4,790,303 A | 12/1988 | Steffee | |
| 4,802,468 A | 2/1989 | Powlan | |
| 4,820,305 A | 4/1989 | Harms et al. | |
| 4,834,757 A | 5/1989 | Brantigan | |
| 4,842,517 A | 6/1989 | Kawahara et al. | |
| 4,863,430 A | 9/1989 | Klyce et al. | |
| 4,863,474 A | 9/1989 | Brown et al. | |
| 4,877,020 A | 10/1989 | Vich | |
| 4,878,915 A | 11/1989 | Brantigan | |
| 4,904,260 A | 2/1990 | Ray | |
| 4,904,261 A | 2/1990 | Dove et al. | |
| 4,927,421 A | 5/1990 | Gable et al. | |
| 4,936,848 A | 6/1990 | Bagby | |
| 4,936,851 A | 6/1990 | Fox et al. | |
| 4,950,270 A | 8/1990 | Bowman et al. | |
| 4,961,740 A | 10/1990 | Ray et al. | |
| 5,015,247 A | 5/1991 | Michelson | |
| 5,015,255 A | 5/1991 | Kuslich | |
| 5,026,373 A * | 6/1991 | Ray et al. | 606/61 |
| 5,055,104 A | 10/1991 | Ray | |
| 5,059,193 A | 10/1991 | Kuslich | |
| 5,062,845 A | 11/1991 | Kuslich et al. | |
| 5,134,499 A | 7/1992 | Sata et al. | |
| 5,139,499 A | 8/1992 | Small et al. | |
| 5,147,402 A | 9/1992 | Bohler et al. | |
| 5,195,541 A | 3/1993 | Obenchain | |
| 5,263,953 A | 11/1993 | Bagby | |
| 5,300,076 A | 4/1994 | Leviche | |
| 5,313,962 A | 5/1994 | Obenchain | |
| 5,354,292 A | 10/1994 | Braeuer et al. | |
| 5,354,302 A | 10/1994 | Ko | |
| 5,357,983 A | 10/1994 | Mathews | |
| 5,358,511 A | 10/1994 | Gattuma et al. | |
| 5,370,697 A | 12/1994 | Baumgartner | |
| 5,400,805 A | 3/1995 | Warren | |
| 5,423,817 A | 6/1995 | Lin | |
| 5,425,772 A * | 6/1995 | Brantigan | 623/17.11 |
| 5,425,773 A | 6/1995 | Boyd et al. | |
| 5,439,464 A | 8/1995 | Shapiro | |
| 5,443,514 A * | 8/1995 | Steffee | 128/898 |
| 5,445,639 A | 8/1995 | Kuslich et al. | |
| 5,454,811 A | 10/1995 | Huebner | |
| 5,458,638 A * | 10/1995 | Kuslich et al. | 623/17.11 |
| 5,470,334 A | 11/1995 | Ross et al. | |
| 5,480,403 A | 1/1996 | Lee et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,534,031 A * | 7/1996 | Matsuzaki et al. | 623/17.11 |
| 5,554,191 A | 9/1996 | Lahille et al. | |
| 5,609,636 A | 3/1997 | Kohrs et al. | |
| 5,683,463 A * | 11/1997 | Godefroy et al. | 623/17.16 |
| 5,906,616 A * | 5/1999 | Pavlov et al. | 606/247 |
| 6,093,207 A * | 7/2000 | Pisharodi | 623/17.16 |

FOREIGN PATENT DOCUMENTS

| | | |
|---|---|---|
| DE | 36 20 549 A1 | 12/1987 |
| EA | 0 260 044 A1 | 6/1988 |
| EA | 0 269 176 A2 | 6/1988 |
| EP | 0 73 177 A2 | 3/1983 |
| EP | 0 260 222 A2 | 3/1988 |
| EP | 0 269 175 A2 | 6/1988 |
| EP | 0 307 241 | 3/1989 |
| EP | 0 551 187 S | 7/1993 |
| EP | 0 637 440 | 2/1995 |
| ES | 283078 | 5/1985 |
| FR | 2295729 | 7/1976 |
| FR | 2710519 | 4/1995 |
| JP | S56-34731 | 4/1981 |
| JP | 57-29348 | 2/1982 |
| JP | 58-78653 | 5/1983 |
| JP | 61-135652 | 6/1986 |
| JP | S 62-501129 | 5/1987 |
| JP | 62-164458 | 7/1987 |

| JP | 63-43654 | 2/1988 |
| JP | S 63-158045 | 7/1988 |
| JP | 1-502402 | 8/1989 |
| JP | 1-314560 | 12/1989 |
| JP | H 3-503133 | 7/1991 |
| WO | WO-87/07827 | 12/1987 |
| WO | WO-88/03781 | 6/1988 |
| WO | WO-89/12431 | 12/1989 |
| WO | WO-90/00037 | 1/1990 |
| WO | WO-91/06261 | 5/1991 |
| WO | WO-94/17759 | 8/1994 |

OTHER PUBLICATIONS

Kiyoshi Kaneda and Isao Yamamoto, "Spinal Instrumentation Surgery in Lumbar and Lumbosacral Spine," The Improvement of Medicine, vol. 147, No. 14, Dec. 31, 1988.

Hiroshi Yamamoto, "Spinal Instrumentation for Lumbar Spine—Segmental Transverse Wiring For Spondylolysis and Pedicular Screw-Spinal Plate for Spondylolisthesis," The Improvement of Medicine, vol. 145, No. 1, Apr. 2, 1988.

Kenichiro Shibata, Masayoshi Oga, Kazuo Hayashi, Yoichi Sugioka, "A new Contrivance of Anterior Spinal Fusion in Cervical Spine," Orthopaedic and Traumatic Surgery, vol. 35, No. 3, pp. 811-813, 1987.

Haruo Tsuji, "Anterior Body Fusion of Lumbar Spine Hernia," Operation, vol. 41, No. 11, pp. 1803-1811, 1987.

Hirotugu Oda, Shinya Kawai, Tetsuro Murakami et al., "Osteoplastic Hemi-Bilateral Partial Laminectomy of Lumbar Spinal Hernia," Operation, vol. 41, No. 11, pp. 1785-1791, 1987.

T. Yano et al., "Treatment of Spondylolisthesis By Posterior Fusion With Bone Grafting To Neural Arch Defect," Clinical Orthopaedic Surgery, vol. 17, No. 4, pp. 394-399, 1982.

T. Yamane et al, "A Case Report of Multiple Lumbar Spondylolyses with Spondylolistheses," Clinical Orthopaedic Surgery, vol. 23, No. 3, pp. 311-314, 1988.

M. Maeshiro, K. Otani, K. Shibasaki, S. Nakai, K. Nemoto, M. Yoshida, "Posterior Fracture-Dislocation of the Thoracic Spine: Two Cases Report," Orthopedic Surgery, vol. 39, No. 9, pp. 1973-1377, 1988-9.

Kunio Takaoka; "Clinical Application of Ceramic Implants In Orthopedics Surgery," Medicina Philosophica, vol. 4, No. 7, pp. 546-552, 1985.

"Intervertebral Body Fusion By the Use of Posterior Bone Dowel," by Benjamin R. Wiltberger, M.D., Clinical Orthopaedics, 35:69-79, 1964.

"Gewebsreaktion auf ein Titan-Hohlzylinderimplantat mit Titan-Spirtzschichtoberflache", by A. Schroeder, O. Pohler and F. Sutter, Separatdruck aus: Schweiz. Mschr. Zahnheilk, vol. 86, No. 7, pp. 713-727, 1976.

"Osseointegrated Titanium Implants, Requirements for Ensuring a Long-Lasting Direct Bone-To-Implant Anchorage in Man", By T. Albrektsson et al. Acta orthop. scand. vol. 52, pp. 155-170, 1981.

"The Reactions of Bone, Connective Tissue and Epithelium to Endosteel Implants With Titanium-Sprayed Surfaces", by A. Schroeder et al. J. Max.fac.Surg. 9, pp. 15-25, 1981.

"Neue Rekonstruktionsmoglichkeiten Bei Unterkeiferdefekten nach Tummorresektion", by J. Raveh et al., Separatdruck aus:Schweiz, Mschr. Zahnheilk. vol. 91, Nor. 11, p. 899-920, 1981.

"Cementless Fixation of Polyethylene Acetabular Component in Total Hip Arthroplasty", By E. W. Morscher et al., Archives of Arthropaedic and Traumatic Surgery, vol. 99, Issue 4, pp. 223-230, 1982.

"Neue Rekonstruktionsmoglichkeiten des Unterkeifers bei knochemen Defekten nach Tumorresektionen" by J. Raueh et al., Chirurg, vol. 53, pp. 459-467, 1982.

"New Concepts in the Reconstruction of Mandibular Defects Follwing Tumor Resection", by Y. Reveh, M.D., DMD, et al. J. Oral Maxillofax Furg. vol. 41, Issue 1, pp. 3-16, Jan. 1983.

Cervical Vertebral Interbody Fusion in the Horse: A Comparative Study of Bovine Zenografts and Autogranfs Supported by Stainless Steel Baskets:, by R. MN. Debowes et all, 29th Annual ORS, Anaheim, CA, Mar. 8-10, 1983, p. 407 and 1 page of figures.

"Percutaneous Lateral Discectory of the Lumbar Spine", by P. Kambin, M.D. et al. Clinical Orthopaedics, vol. 174, pp. 127-131, Apr. 1983.

"Use of the Titanium Coated Hollow Screw and Reconstruction Plate Systemin Bridging Lower Jaw Defects", by J. Ravey et al. J Oral Maxillofac Surg., vol. 42, Issue 5, pp. 281-294, May 1984.

"Titanplasma-beschichtetes Holschrauben- under Rekonstruktionsplatten-System (THRP) zue Uberbruckung von Kieferdefekten", by F. Sutter et al. Chirurg. vol. 55, Issue 1, pp. 741-748 Nov. 1984.

"Titanplasma-beschichtetes Holschrauben- under Rekonstruktionsplatten-System (THRP) zue Uberbruckung bond Kidferdefekten", by F. Sutter et al. Chirurg. vol. 56, Issue 5, pp. 337-344, May 1985.

"Anterior Cervical Interbody Fusion With Threaded Cylindrical Bone", by Jose M. Otero Vich, M.D. , J. Neurosurg. vol. 63, pp. 750-753, Nov. 1985.

"Due vordere Verplattung der Halswirbelsaule mit dem Holschrauben-Plattensystem aus Titanium" by E. Morscher et al. Chirurg. vol. 57, Issue 11, pp. 702-707, 1986.

"Surgical Procedures for Reconstruction of the Lower Jaw Using the Titanium-0Coated Hollow-Screw Reconstruction Plate System: Bridging of Defects", by J. Raven et al. The Ololaryngologic Clinics of North America, vol. 20, No. 3, pp. 535-558, Aug. 1987.

"Titanium Coated Hollow Screw and Reconstruction Plate System for Bridging of Lower Jaw Defects: Biomechanical Aspects", by F. Sutter et al. Int. J. Oral Maxillofac. Surg. vol. 17, Issue 4, pp. 267-274, 1988.

"Arthrodesis By the Distraction-Compression Method Using a Stainless Steel Implant" by George W. Bagby, M.D. M.S. Orthopedics, vol. 11, pp. 931-934, Jun. 1988.

"Engineering and Design Aspects of theI>T>I> Hollow-Basket Implants" by F. Sutter, D.D.S. et al., Journal of Oral Implantology, pp. 535-551, 1983.

"Methods of Lumbar Fusion", Norman W. Hoover, M.D., The Houmal of Bone and Joint Surgery, Jan. 1968, pp. 194-210.

"Anterior Discectomy and Interbody Fusion for Lumbar Disc Herniation", Shun-Echi Inque, M.D. Ph.D. et al., Lumbar Disc Herniation, vol. 183, Mar. 1984, pp. 22-31.

"Interspace Distraction and Graft Subsedence After Anterior Lumbar Fusion With Femoral Strut Allograft", Spine vol. 18, No. 16, pp. 2392-2400, 1993.

"Normal Sagittal Alignment" Keith H. Bridwell, M.D., Federation of Spine Associations, Section IV—Scoliosis Research Society, Sagittal Spinal Balance—Symposium No. 1, Feb. 27, 1994.

"A Technique for Posterior Lumbar Interbody Fusion" Charles G. hUtter, Chapter 19, Lumbar Interbody Fusion, 1989, pp. 227-232.

* cited by examiner

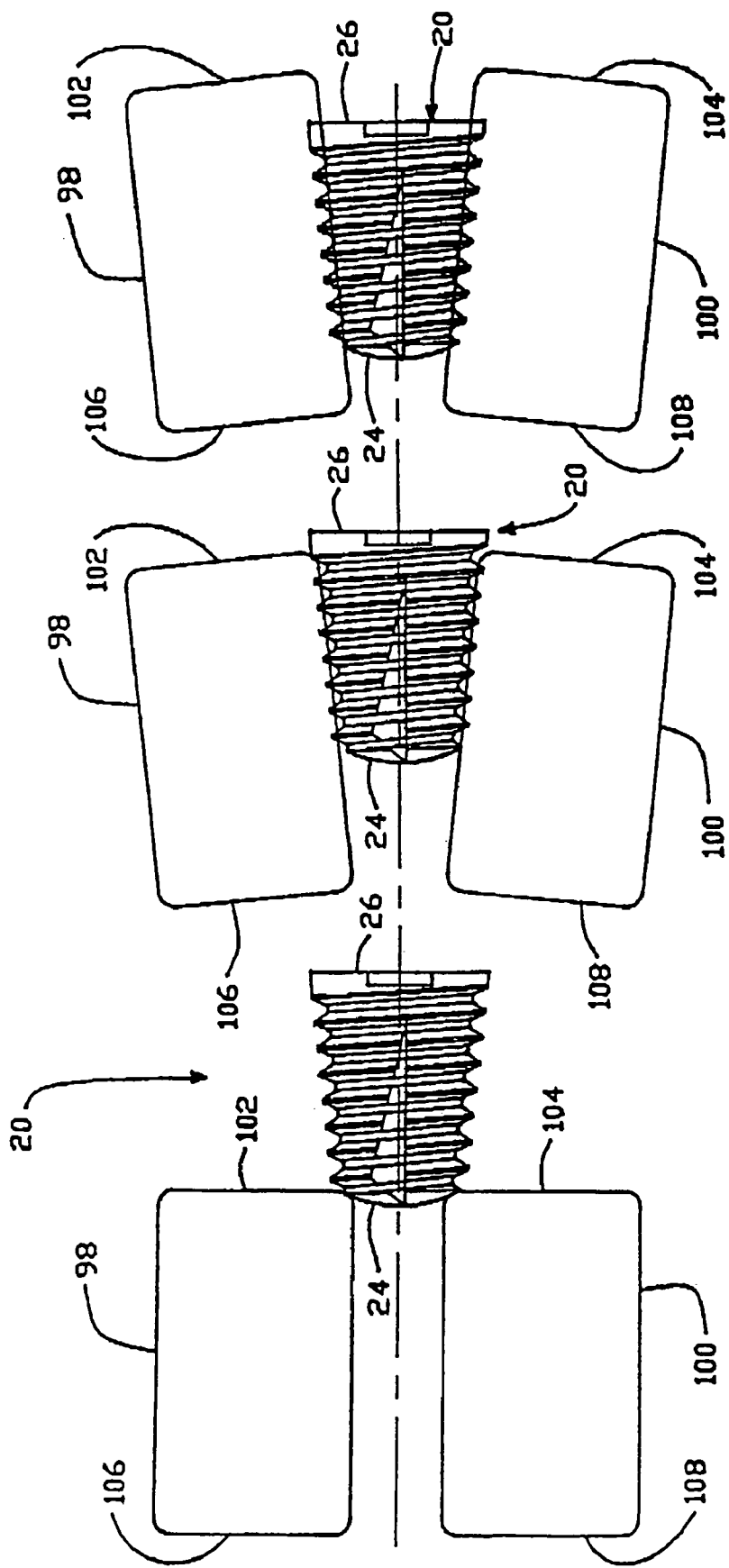

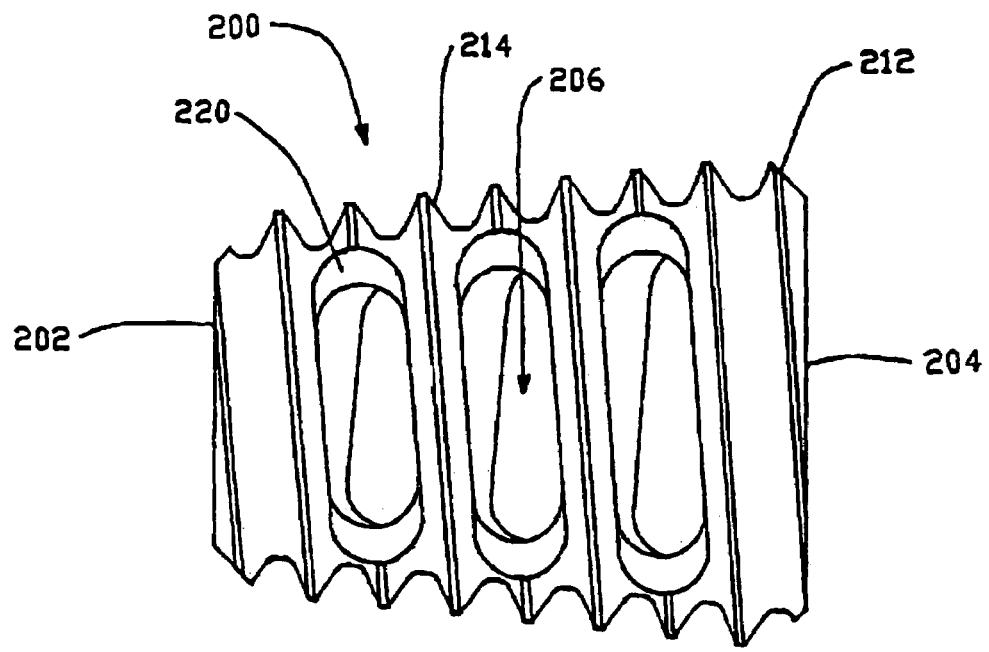
FIG.—10
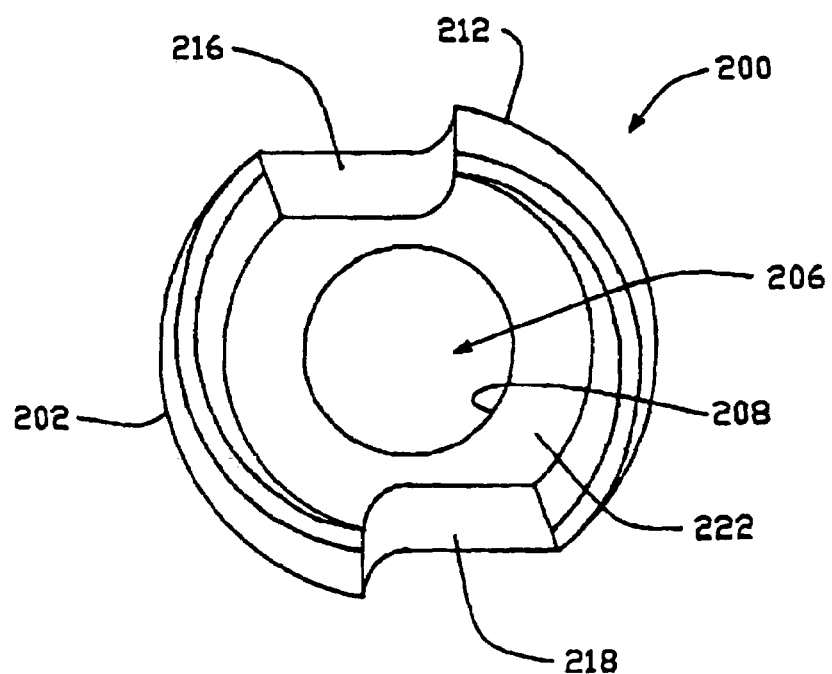
FIG.—11

METHODS OF INSERTING CONICALLY-SHAPED FUSION CAGES

CROSS REFERENCE TO RELATED APPLICATIONS

The present invention is a continuation of U.S. patent application Ser. No. 10/350,834, filed Jan. 24, 2003, which is a continuation of U.S. patent application Ser. No. 09/358,188, filed Jul. 20, 1999, abandoned, which is a continuation of U.S. patent application Ser. No. 08/781,525, filed Jan. 9, 1997, abandoned, which is a file wrapper continuation of U.S. patent application Ser. No. 08/306,879 filed Dec. 15, 1994, abandoned. The disclosures of the '834, '188, '525 and '879 applications are hereby incorporated by reference herein.

BACKGROUND OF THE INVENTION

This invention is directed to devices and methods for facilitating the fusing of bone structures and more particularly the fusing together of adjacent vertebral bodies or bone structures.

Technical literature and patent documents disclose a number of devices and methods for fusing bones together. One such device which has proven to be successful is disclosed in U.S. Pat. No. 4,961,740, entitled "V-THREAD FUSION CAGE AND METHOD OF FUSING A BONE JOINT," which patent has been assigned the present assignee and which patent is incorporated herein by reference. The referenced patent discloses a fusion cage which is preferably cylindrical and has threads formed as part of the external cylindrical surface. The fusion cage defines an internal cavity and apertures through the wall of the cage which communicate the external cylindrical surface with the internal cavity. The apertures are formed in the valleys of the threads. Normally two such cages are used to stabilized and fuse together adjacent vertebral bodies or bone structures.

In practice, using a posterior approach, a patient's vertebral bone structures are exposed and degenerate disk material located between the vertebral bone structures is removed. A threaded tap is used to tap complementary threads in the upper and lower vertebral bone structures preparatory to the insertion of the above fusion cage. Once such tapping has been accomplished, using an introduction tool, the fusion cage is screwed into the space between the adjacent vertebral bone structures. The threads bite into the bone of the upper and lower vertebral bone structures, stabilizing the bone structures, and preventing the fusion cage from working out of this position due to patient movement. Generally two such fusion cages are applied using this technique. Once the two implants have been positioned, then bone growth inducing substances, such as bone chips, are packed into the internal cavity of the fusion cages. These bone growth inducing substances come into immediate contact with the bone from the vertebral bone structures which project into the internal cavity through the apertures. Such projection of bone is due to the fact that the apertures are formed in the valleys of the external threads of the fusion cage. Such immediate bone to bone contact between the vertebral bone structures and the bone pack within the fusion cages results in more rapid propagation of bone cells between the adjacent vertebral bone structures and thus a more rapid fusion of the adjacent vertebral bone structures.

SUMMARY OF THE INVENTION

The present invention is directed to a fusion cage which has been designed to be implanted using an anterior approach to the vertebral bone structures.

In a first embodiment of the present invention, the fusion cage includes a conically-shaped cage body having a proximal end and a distal end, said distal end having a diameter which is smaller than the diameter of the proximal end. The distal end further is rounded with for example a bull nose in order to facilitate the insertion of the cage body relative to one or more bone structures. The conically-shaped cage body is particularly advantageous for use with an anterior approach to vertebral bone structure fusion. This is due to the fact that the normal lordosis of the vertebral bone structures defines a wedged-shape space for a vertebral disk between, for example, lumbar vertebrae. Accordingly, the conically-shaped body cage can be sized and selected in order to maintain or enlarge upon the normal lordosis.

In a second embodiment of the present invention, a fusion cage includes a conically-shaped cage body having a proximal end and a distal end with the distal end having a diameter which is smaller than the diameter of the proximal end. The conically-shaped cage body has a conically-shaped outer surface and at least one flute formed in the conically-shaped outer surface. The flute acts as a relief much as the flute placed on self-tapping screws in order to facilitate the insertion of the fusion cage using a twisting motion between two vertebral bone structures.

In a third embodiment of the invention, a fusion cage includes a conically-shaped cage body having a proximal end and a distal end, the distal end having a diameter which is smaller than the diameter of the proximal end. The conically-shaped cage body has a conically-shaped outer surface and a plurality of threads formed as part of the conically-shaped outer surface. The plurality of threads allows the cage body to be inserted using an anterior approach. Due to the fact that the cage body is conically-shaped, the requirement for pre-tapping the vertebral bone structures to receive the fusion cage is eliminated with the fusion cage being self-tapping. Also the cage gradually spreads apart the vertebral bone structures as the cage is inserted in order to regain or enlarge the natural lordosis of the adjacent vertebral bone structures. As with other embodiments of the present invention, flutes can be provided through the plurality of threads in order to allow for enhanced thread tapping by the cage and for a smoother insertion of the fusion cage between the vertebral bone structures. Preferably two or three flutes would be formed spaced about the fusion cage in order that one flute would be engaging with or adjacent to an upper vertebral bone structures with another flute being engaging with or adjacent to a lower vertebral bone structure. Such a relationship maintains alignment of the fusion cage and prevent wandering as the fusion cage is introduced between the two vertebral bone structures. Without two or more flutes, wandering might occur due to the fact that the threads are only substantially engaged with the vertebral bone structures and not with the disk material between the vertebral bone structures, which disk material does not provide support to the threads.

In a further aspect of the invention, any of the above embodiments can be provided with a plurality of apertures through the fusion cage and an internal cavity with the apertures communicating between the internal cavity and the external surface of the fusion cage. Bone growth inducing substances, such as bone chips, can be packed into the internal cavity either before the fusion cage is inserted or after the fusion cage has reached a final insertion position. The bone chips come in contact with the vertebral bone structures through the apertures in order to facilitate fusion between the adjacent vertebral bone structures.

In another aspect of the invention which can be included in any of the above embodiments, the cage body can have a round or bull nose distal end with one or more flutes formed in the round or bull nose distal end in order to enhance the self-tapping nature of the fusion cage.

In yet another aspect of the invention, introduction tools allow the fusion cage to be accurately positioned between the vertebral bone structures.

The method of the present invention affords access to adjacent vertebral bone structures using an anterior approach and procedure. Such anterior approach and procedure can be preferably performed laparoscopically using an introduction set including a cannula. A laparoscopic procedure is minimally invasive as the abdomen muscle tissue can be spread using a set of cannula of increasing size and a small opening thereby developed through which a fusion cage can be inserted. Such a procedure is less traumatic to the tissue than an alternate anterior approach and procedure, also known as an anterior lumbar interbody fusion, where an incision, perhaps up to five inches long is made, through the abdomen muscle tissue. It is to be understood however that either anterior approach and procedure can be used with the fusion cage and fall within the scope of the invention.

After such access, using preferably a laparoscopic technique, degenerate disk material can be removed and, using a cannula and insertion tool, an appropriately shaped fusion cage can be screwed into place between the vertebral bone structures in order to stabilize the vertebral bone structures and allow for fusion. Either preparatory to insertion of the fusion cage or after it has been inserted, bone chips or other bone growth inducing substances can be inserted into the fusion cage to promote bone to bone contact and subsequent fusion.

It is to be understood that although the above embodiments have been described with respect to the fusion of adjacent vertebral bodies or bone structures, that the present invention can be used to fuse together a variety of bone structures, in addition to being fused to one bone structure and used as, for example, a base for an implant.

Other objects and advantages of the invention can be obtained through a review of the specification and the figures.

BRIEF DESCIPTION OF THE FIGURE

FIGS. 7, 8, and 9 depict progressive stages in the method of inserting the fusion cage between adjacent vertebral bone structures.

FIG. 10 depicts a side view of an alternative embodiment of the fusion cage of the invention.

FIG. 11 depicts the left end (distal end) view of the fusion cage of FIG. 10.

Figure 12:
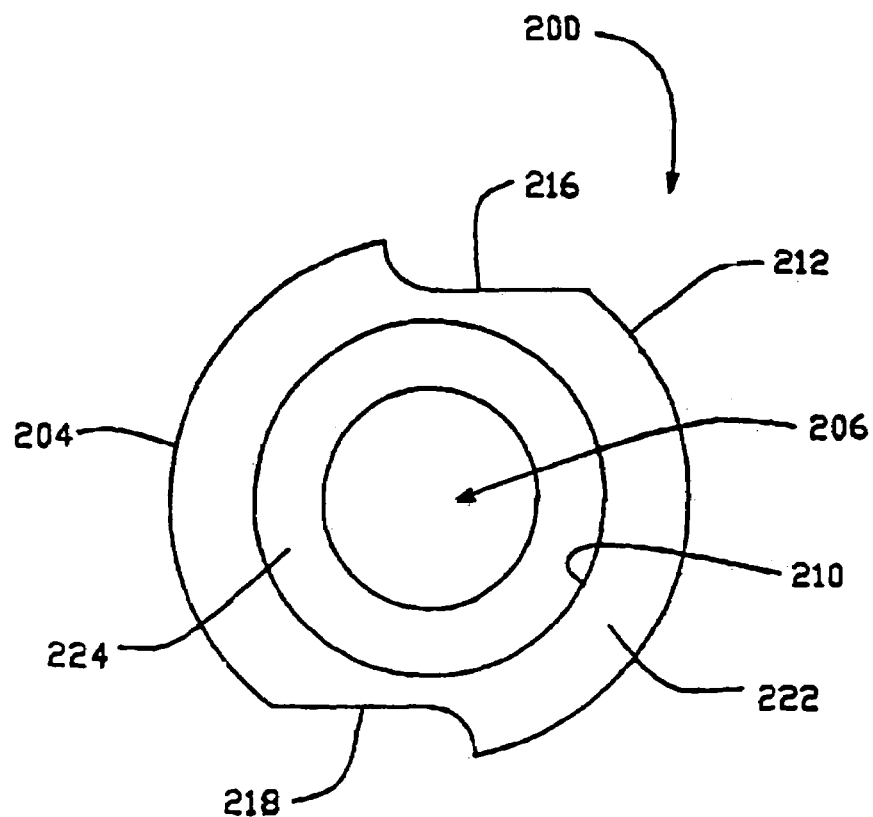

FIG. 12 depicts the right end (proximal end) view of the fusion cage of FIG. 10.

Figure 13:
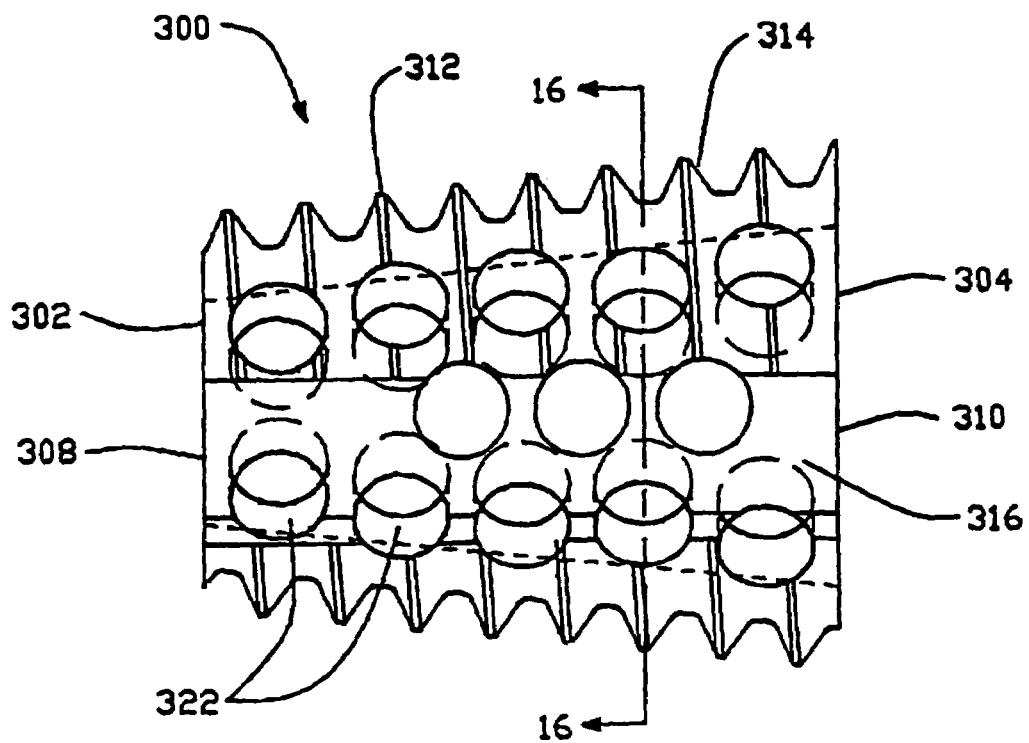

FIG. 13 depicts a side view of yet another embodiment of the fusion cage of the present invention.

Figure 14:
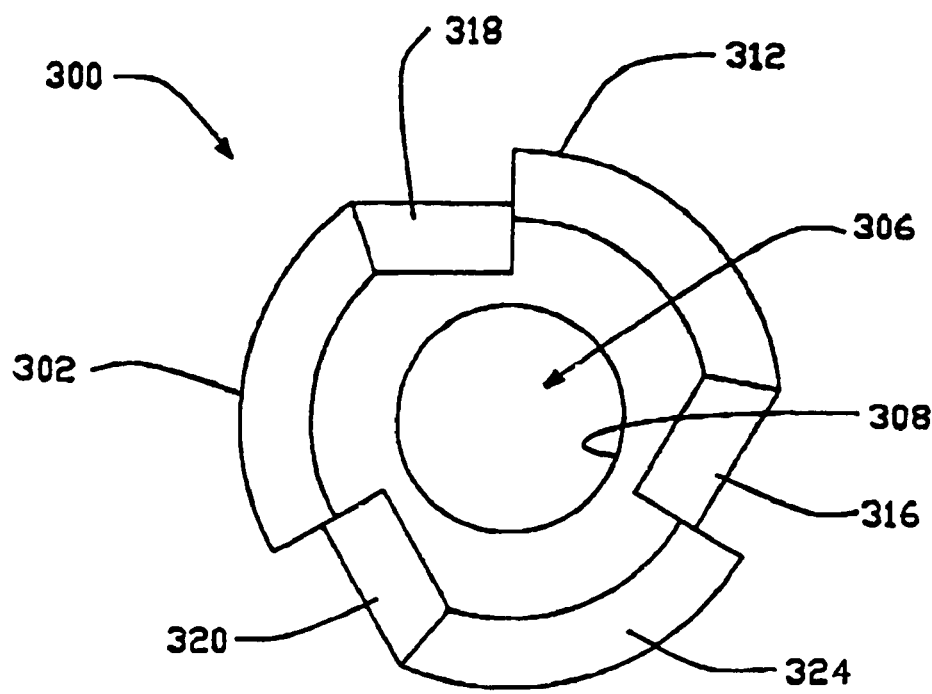

FIG. 14 depicts a left distal end (distal end) view of the fusion cage of the invention of FIG. 13.

Figure 15:
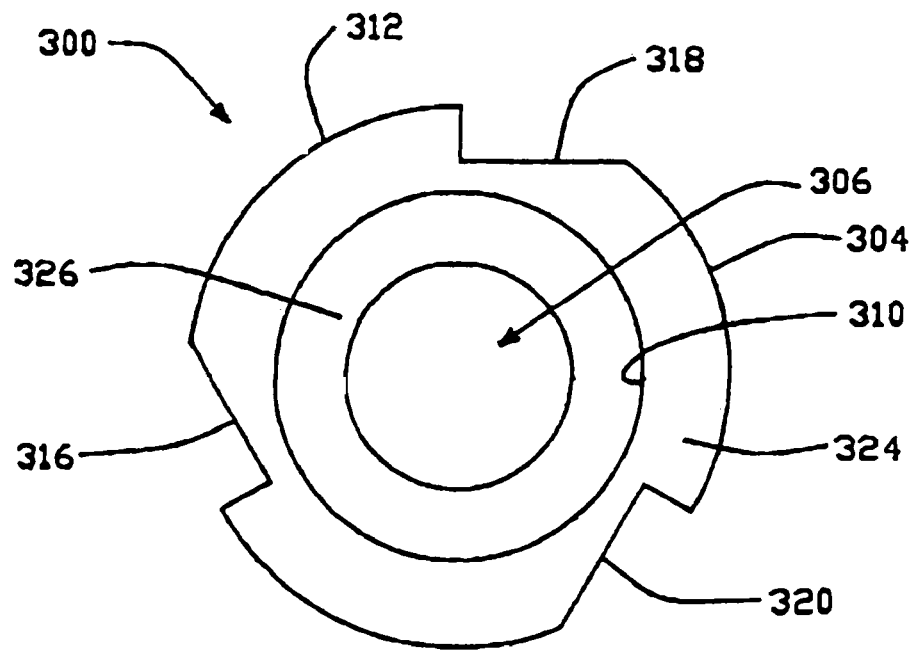

FIG. 15 depicts a right end (proximal end) view of the fusion cage of the invention of FIG. 13.

Figure 16:
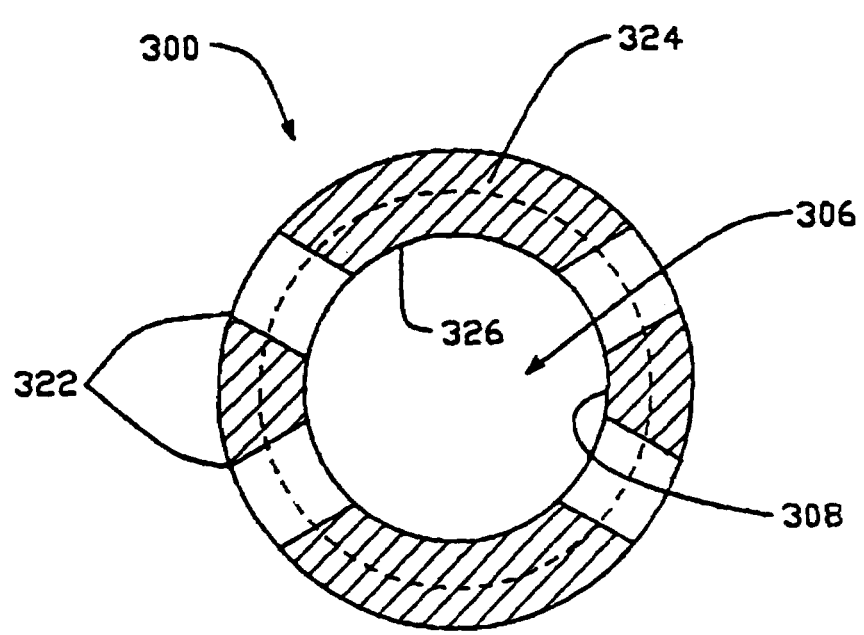

FIG. 16 depicts a sectional view taken through line 16-16 of FIG. 13.

DETAILED DESCRIPTION

Figure 1:
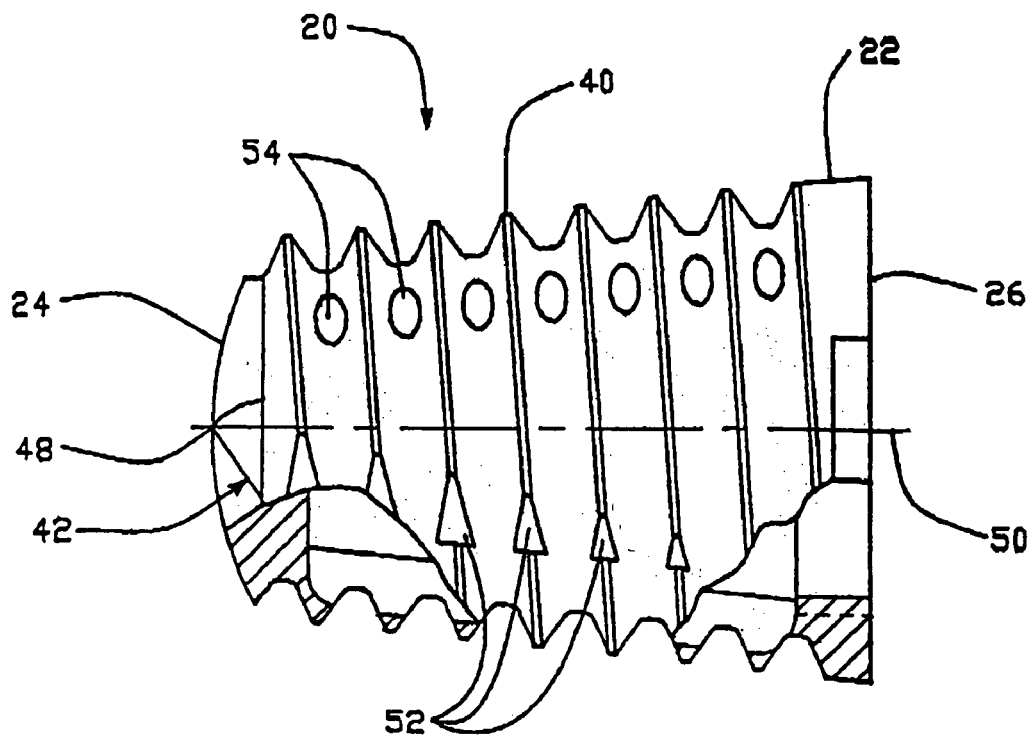
FIG. 1 is a partially sectional side view of an embodiment of the fusion cage of the invention.
Figure 5:
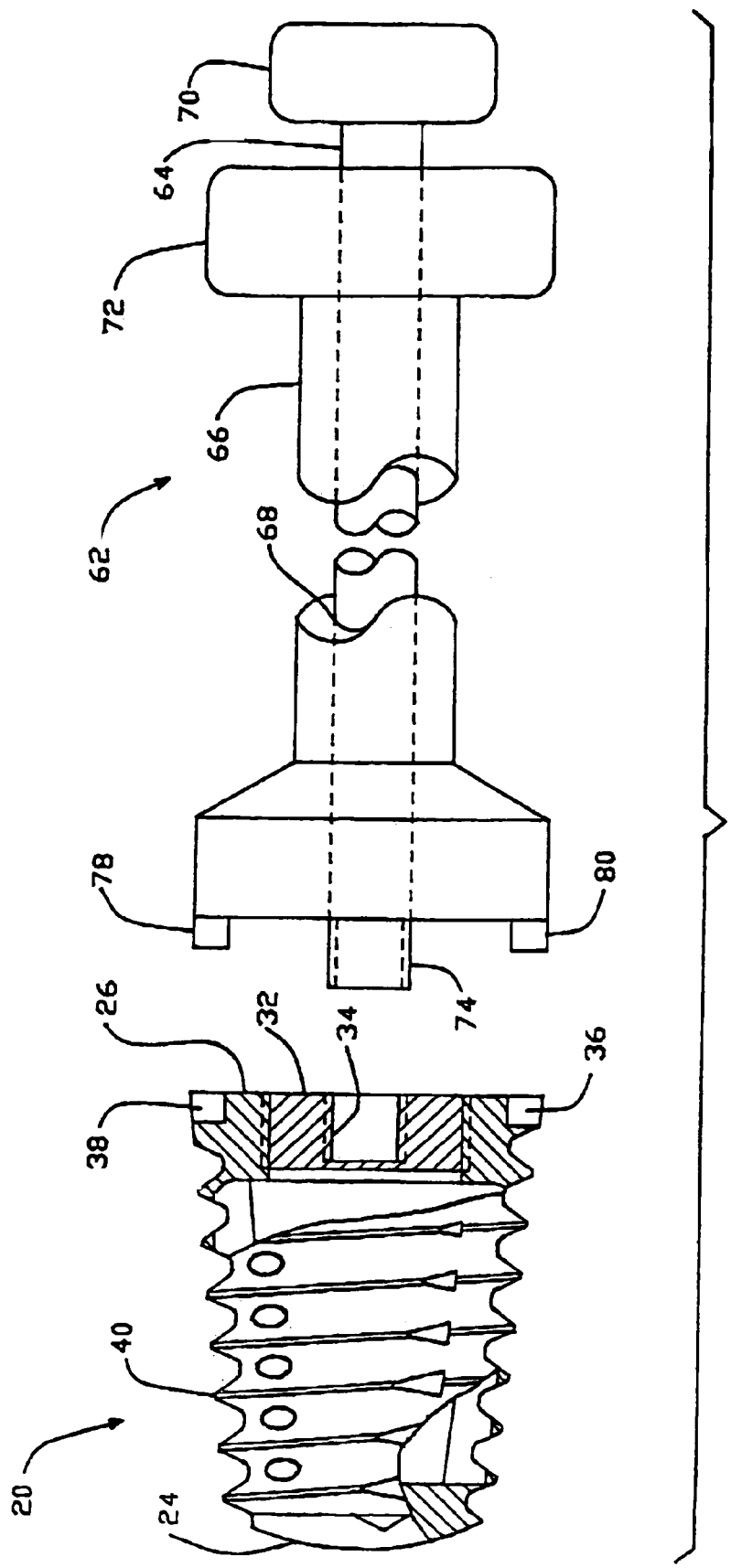
FIG. 5 depicts fusion cage of FIG. 1 in conjunction with an introduction tool.

With respect to the figures in a particular FIG. 1, a side view of the preferred embodiment of the fusion cage 20 is depicted. Fusion cage 20 includes a fusion cage body 22 which in this preferred embodiment is provided in the shape of a cone. Fusion cage 20 includes a distal end 24 and a proximal end 26. The distal end 24 in a preferred embodiment is rounded or bull nosed in order to facilitate the insertion of the fusion cage 20 relative to one or more bone structures. The proximal end 26 includes an opening 28 which communicates with an internal cavity 30 defined by the fusion cage 20. The opening 28 in a preferred embodiment is threaded so that it can receive an end cap or plug 32 (FIG. 5). End cap 32 is used to close off the proximal end 26 and retain bone growth inducing substances packed therein as described hereinbelow. As can be seen in FIG. 5, end cap 32 includes a threaded bore 34 which is designed to receive an insertion tool. The threaded bore 34 has an initial unthreaded, hex-shaped section 35 which can be used with a socket wrench to tightly position end cap 32 in opening 28. The proximal end 26 further define first and second peripheral indentations 36, 38. These peripheral indentations 36, 38 receive tangs from an insertion tool as described hereinbelow for facilitating the insertion of the fusion cage 20.

A plurality of threads 40 is defined as part of the outer cylindrical surface 42 of the body 22. It is to be understood that the plurality of threads can be replaced with a plurality of interrupted or discrete threads or a plurality of projections, ridges, protrusions, barbs, or spurs and be within the spirit and scope of the invention. In certain preferred embodiments, the threads 40 are V-threads as disclosed in U.S. Pat. No. 4,961, 740, the disclosure of which is hereby incorporated by reference herein. The term V-thread means that the crown of the thread is sharp, although its valley may be blunt or rounded to permit the mating peaks of the female threads to have adequate strength. The angle of the crown of the V-thread should be no more than 90° and at least 45° because the pitch would be undesirably small if the angle were smaller.

Figure 2:
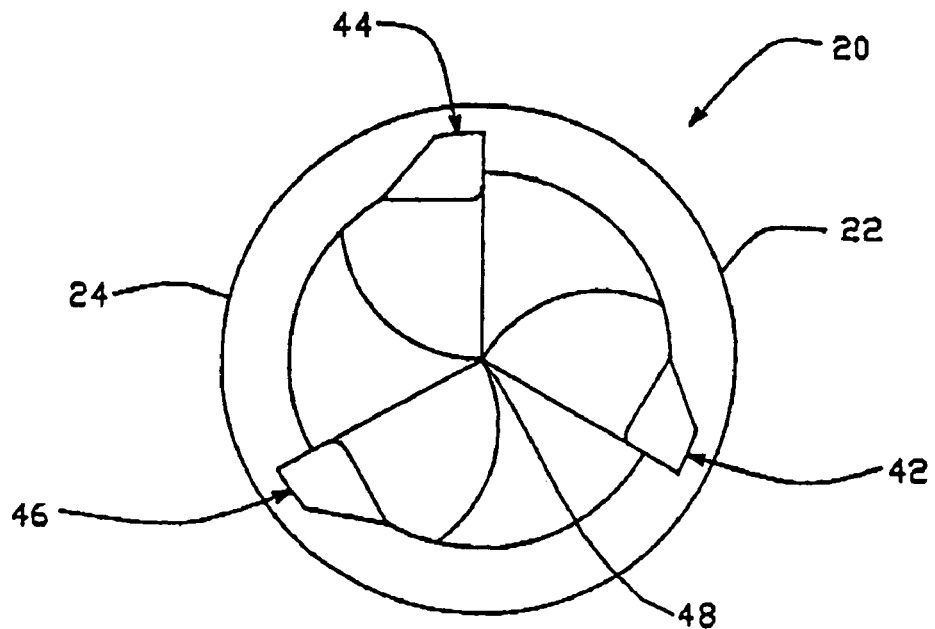
FIG. 2 depicts a left end (distal end) view of the fusion cage of FIG. 1.
Figure 3:
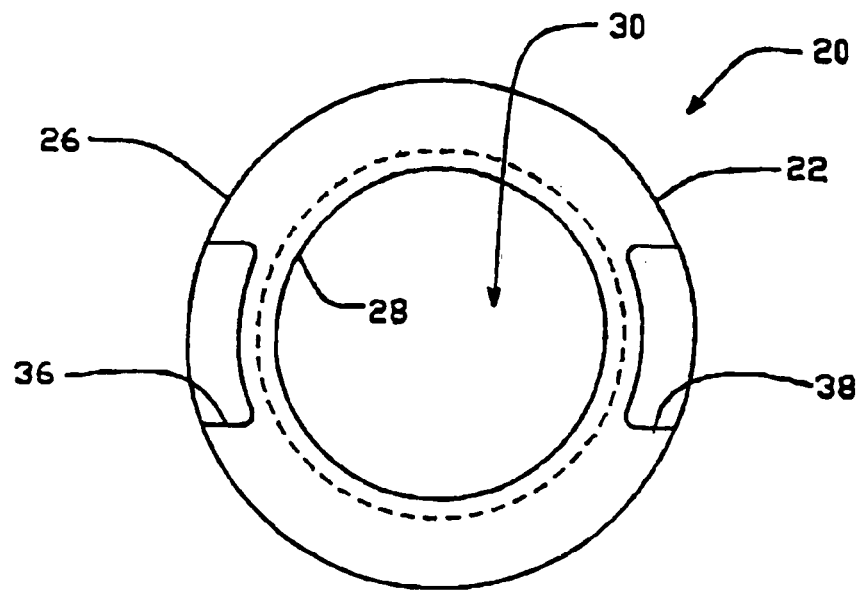
FIG. 3 depicts a right end (proximal end) view of the fusion cage of FIG. 1.

The rounded distal end 24, and at least some of threads 40 defined flutes or relief grooves 42, 44, and 46. (FIGS. 1, 2.) In a preferred embodiment, flutes 42, 44, and 46 meet at a central point 48 of the distal end 24 on the longitudinal axis 50 of the fusion cage 20. In other embodiments the flutes can be smaller and not extend all the way to the central point 48 on the longitude axis 50. Still in other embodiments, the flutes can be eliminated from the distal end 24 and such embodiments are still within the spirit and scope of the invention. The flutes extend from the distal end 24 toward the proximal end 26 as shown in FIG. 1 with respect to flute 42. These flutes are defined by the sections 52 which are removed from the threads. In a preferred embodiment, the flutes become narrower as they approach the proximal end 26 due to the fact that thread relief for purposes of self-tapping becomes less important as the cage reaches a final resting position. As shown in other embodiments, the flutes can be deeper and extend from the distal end completely to the proximal end. Still further in other embodiments the flutes can be confined to the first several threads adjacent to the distal end and/or to just the distal end.

As can be seen in FIGS. 1-4, a plurality of apertures 54 are provided through wall 56 of the fusion cage 20. In a preferred embodiment, these apertures 54 are formed by broaching grooves 58 in the internal surface 60 of the internal cavity 30. The effect of such broaching is to remove material from the valleys between the threads 40, thus defining the aperture 54. The advantages of such an arrangement are taught by the above-referenced U.S. Pat. No. 4,961,740, which patent is incorporated herein by reference and allows for immediate bone to bone contact between the vertebral bodies or bone structures and the bone packed within the internal cavity 30 of the fusion cage 20.

The apertures 54 in a preferred embodiment increase in size from smaller apertures closer to the distal end 24 to a larger aperture closer to the proximal end 26. This increase in size allows for more bone to bone contact. Alternatively in the embodiment as shown in FIG. 1, all the apertures are of the same size.

Figure 4:
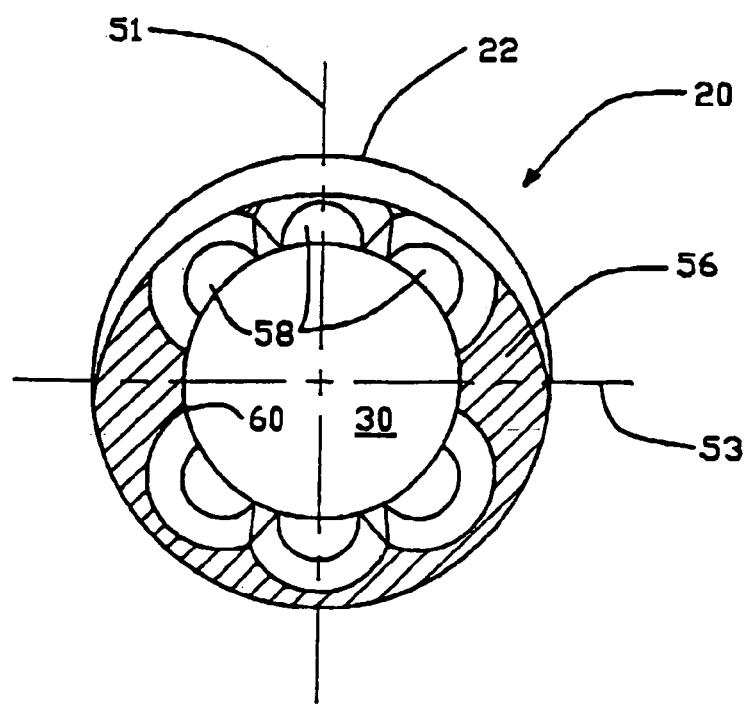
FIG. 4 depicts a view through line 4-4 of the fusion cage of FIG. 1.

As can be seen in FIG. 4, the apertures are clustered about a transverse axis 51, both at the upper and lower end of the axis. This is so that in position, the apertures come into contact with the upper and lower vertebral bone structures (FIG. 9) to encourage bone growth through the fusion cage from the vertebral bone structures. The lateral section of the fusion cage found along the other transverse axis 53 do not have apertures in order to prevent growth of disk material which might interfere with the bone fusing process.

A preferred embodiment of the conically-shaped fusion cage 20 includes a fusion cage that is 23 millimeters in length having a distal end 24 with a diameter of 14 millimeters and a proximal end 26 with a diameter of 18 millimeters. The cage body is a right circular cone. The threads have a pitch of 300 and there are ten threads per inch with a thread depth of 0.053 inches. Further the cage is made of a titanium material. Preferably this and the other disclosed fusion cages disclosed are machined. However, the processes such as molding can be used to accomplished formation of the fusion cages.

The cage is inserted between vertebral bodies using an insertion tool 62 (FIG. 5). Insertion tool 62 includes an inner handle 64 and an outer handle 66. The outer handle includes a bore 68 for receiving the inner handle 64. Handles 64, 66 include knobs 70, 72 respectively. The distal end of inner handle 64 defines a threaded shaft 74, having a reverse thread to facilitate easy removal, and the distal end of handle 66 define a cylindrical disk 76 which has first and second tangs 78, 80, projecting from the peripheral edge of the cylindrical disk 76. These tangs 78, 80 are designed to mate with the peripheral indentation 36, 38 of the fusion cage 20. For purposes of inserting the fusion cage between the vertebral bodies, the end cap 32 is inserted into the fusion cage 20 as shown in FIG. 5. Then the threaded shaft 74 of the inner handle is introduced into the threaded bore 34 of the end cap 32. After this is accomplished, the outer handle 66 is slid over the inner handle 64 and the tangs 78, 80 are positioned into engagement with the indentations 36, 38. In this arrangement, the fusion cage 20 can be anteriorly inserted into the space between the vertebral body structures using the insertion tool 62.

Figure 6:
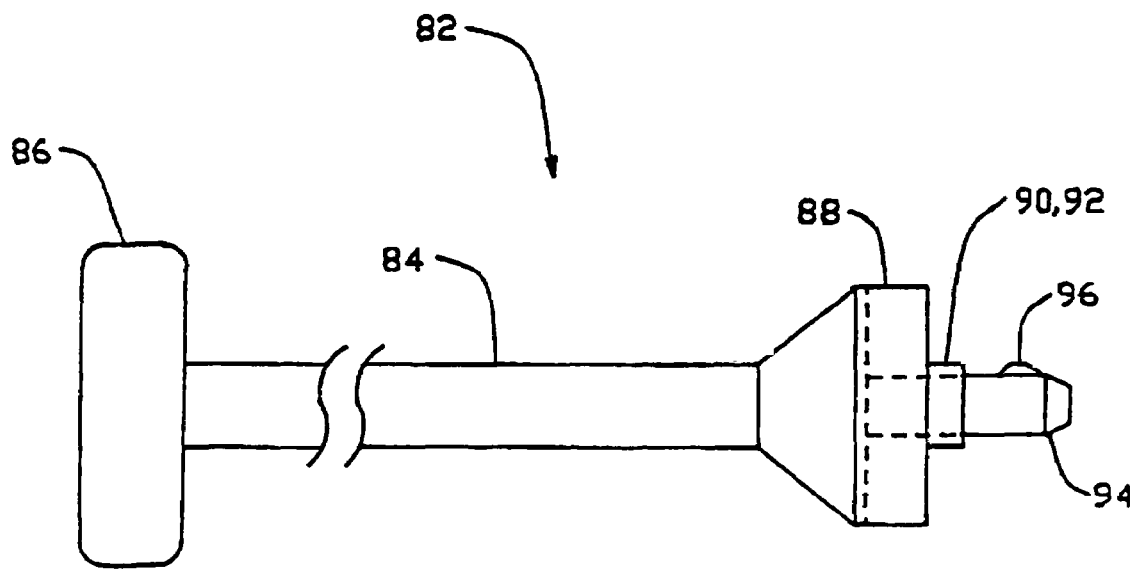
FIG. 6 depicts an alternative embodiment of the introduction tool.

An alternative embodiment of the insertion tool is shown in FIG. 6. In this figure, insertion tool 82 includes a handle 84 with a knob 86. At the end of the insertion tool 82 distal from the knob 86 is a cylindrical disk 88 which has first and second tangs 90, 92, which have the same function as the above tangs 78, 80. Extending from the center of the cylindrical disk 88 along the centerline of the insertion tool 82 is a shaft 94 which has a ball detent 96. For use with insertion tool 82, the threaded bore 34 of the end cap 32 would be replaced with a bore having a lip which could engage with the ball detent 96 of the insertion tool 82.

The method for inserting the fusion cage 20 of FIG. 1 using an anterior approach and procedure to the vertebral bodies is as follows. It is to be understood that although the focus of this discussion is on a laparoscopic procedure, that the anterior approach and procedure can also include a more invasive procedure where a long incision is made in the abdomen wall.

With an anterior approach, using an introduction set such as described by way of example only, in U.S. Pat. No. 4,863, 430, entitled "INTRODUCTION SET WITH FLEXIBLE TROCAR WITH CURVED CANNULA," which is incorporated by reference, but however with larger diameter instruments, an amount of disk material is removed between the two vertebral bodies or bone structures which are to be fused together. This procedure is accomplished through a cannula position adjacent to the vertebral bone structures. With the same or a larger diameter cannula, the fusion cage 20 can be introduced adjacent to the vertebral bone structures. In a first procedure, the fusion cage is packed with bone growth substances and the end cap 32 is affixed to the fusion cage 20. Insertion tool 62 is then secured to the fusion cage 20 and the fusion cage is guided through the cannula to a location adjacent to the upper and lower vertebral body such as presented schematically in FIGS. 7, 8, 9, by upper body 98 and lower body 100. In the initial position as shown in FIG. 7, the fusion cage 20 is adjacent to the anterior surfaces 102, 104 of the vertebral bodies 98, 100. As the introduction tool is turned, the threads 40 of the fusion cage 20 bite into the vertebral bodies 98, 100. Further turning of the introduction tool causes the fusion cage to move through the position shown in FIG. 8 to the final resting position shown in FIG. 9, where the distal end 24 is moved adjacent to the posterior sections 106, 108 of the vertebral bone structures 98, 100. As this occurs, the fusion cage 20 increases the lordosis or spacing between the vertebral bodies, basically distracting the vertebral bodies and causing the vertebral bodies to pivot about the posterior sections 106, 108, with such posterior sections acting like a hinge. It is noted that most of the distraction occurs adjacent to the anterior sections, but that distractions also occur at the posterior sections where the hinged effect is exhibited. Preferably, the lordosis is increased over the normal lordosis in order to stabilize the vertebral bone structures prior to fusion occurring. Stabilization occurs due to the fact that increased lordosis places additional stress on the anterior longitudinal ligaments which are part of the anatomy holding the vertebral bodies in place.

Once the fusion cage 20 is appropriately positioned, the handle 64 of the insertion tool 62 is unscrewed from the cap 32 and the fusion handle 62 is pulled away from the fusion cage.

An alternative embodiment of a fusion cage 200 is shown in FIGS. 10, 11 and 12. Fusion cage 200 includes a distal end 202 and an a proximal end 204. Fusion cage 200 includes an internal cavity 206. End caps not shown can be used to close the ports 208, 210 of distal and proximal ends 202, 204. A plurality of threads 212 are defined on the external conical surface 214 of the fusion cage 200. Defined by the threads 212 are first and second flutes 216, 218, which in this embodiment extend from the distal end 202 to the proximal end 204. These flutes provide thread relief allowing the fusion cage 200 to be self-tapping.

The fusion cage 200 includes a plurality of elongated apertures 220 which are formed through the side walls of a fusion cage 200. The elongated apertures 202 are formed in such a way that the internal conical surface 214 is spaced away from the internal surface 224 of the internal cavity 206 by the thickness of the sidewall 222.

A further embodiment of the invention is shown in FIGS. 13, 14, 15 and 16. In FIG. 16 the fusion cage 300 has distal and proximal ends 302 and 304 respectively. The fusion cage 300 defines an internal cavity 306, and ports 308 and 310 defined through the distal and proximal ends 302 and 304 respectfully. A plurality of thread 312 is defined as part of the external conical surface 314 of the fusion cage 200. First, second and third flutes 316, 318, and 320, are defined in the threads 312 from the distal end 302 to the proximal end 304. These flutes give the fusion cage 300 an enhanced self-tapping advantage. These flutes are equally spaced about the fusion cage 300 in a manner similar to the flutes of the fusion cage embodiment 20 in FIG. 1.

A plurality of aperture 322 is provided through the external conical surface 314 of the fusion cage 300 and through the side wall 324 opening into the internal cavity 306. Accordingly, at the location of the aperture 322 the external surface 314 is held away from the internal surface 326 by the thickness of the side wall 324.

The present invention affords the advantages of a fusion cage which can be introduced through an anterior approach in order to maintain or increase lordosis between adjacent vertebral bodies. The fusion cage has the advantage of being conically-shaped and self-tapping through the use of external flutes. The flutes additionally assist in keeping the fusion cage aligned and centered as the cage is being inserted between the vertebral bone structures.

Other advantages, aspects, and objects of the invention can be obtained through a review of the claims and the appended figures.

It is to be understood that additional embodiments of the invention can be constructed and fall within the spirit and scope of the claims.

The invention claimed is:

1. A method of promoting fusion of adjacent vertebral bodies comprising:
   providing a conically-shaped cage body having threading on an outer surface thereof and a plurality of apertures extending through said outer surface thereof, said cage body including a leading end having a first diameter and a trailing end having a second diameter that is larger than said first diameter, wherein said apertures increase in size from said leading end toward said trailing end;
   positioning said leading end of said cage body adjacent an intervertebral disc space between an upper vertebral body and a lower vertebral body, wherein said upper and lower vertebral bodies have opposing end faces that define upper and lower limits of said intervertebral disc space;
   while urging said leading end of said cage body into said intervertebral disc space, turning said cage body so that said threading bites into said opposing end faces of said upper and lower vertebral bodies for anchoring said cage body to said upper and lower vertebral bodies.

2. The method as claimed in claim 1, further comprising fully inserting said cage body between said opposing end faces of said upper and lower vertebral bodies so that spacing between said opposing end faces is greater at said trailing end of said cage body than at said leading end of said cage body.

3. The method as claimed in claim 1, wherein said opposing end faces of said upper and lower vertebral bodies have first ends and second ends, and wherein said urging step causes said opposing end faces to pivot about said second ends of said opposing end faces.

4. The method as claimed in claim 1, wherein said opposing end faces of said upper and lower vertebral bodies have first ends and second ends, and wherein said urging step causes greater distraction at said first ends of said opposing end faces than at said second ends of said opposing end faces.

5. The method as claimed in claim 1, wherein said threading is continuous threading that extends between said leading end and said trailing end of said cage body.

6. The method as claimed in claim 1, wherein said cage body has a longitudinal axis extending between said leading and trailing ends thereof and a transverse axis extending in a direction that is substantially perpendicular to said longitudinal axis, and wherein said plurality of apertures are clustered about said transverse axis.

7. The method as claimed in claim 6, further comprising inserting said cage body between said upper and lower vertebral bodies so that said clustered apertures confront said opposing end faces of said vertebral bodies.

8. The method as claimed in claim 1, wherein said cage body includes an internal cavity surrounded by said outer surface of said cage body, the method further comprising providing a bone-growth inducing material in said internal cavity of said cage body.

9. The method as claimed in claim 8, wherein said trailing end of said cage body includes an opening in communication with said internal cavity of said cage body for providing said bone-growth inducing material in said internal cavity of said cage body.

10. The method as claimed in claim 1, wherein said cage body is continuously tapered between said leading end and said trailing end thereof.

11. The method as claimed in claim 1, wherein said leading end of said cage body has a rounded nose.

12. The method as claimed in claim 1, wherein said outer surface of said cage body has at least one flute extending from said leading end toward said trailing end of said cage body.

13. The method as claimed in claim 1, wherein said cage body is devoid of a flange so that said cage body is anchored to said upper and lower vertebral bodies solely by said threading on said outer surface thereof.

14. A method of promoting fusion of adjacent vertebral bodies comprising:
   providing a conically-shaped cage body having an outer surface surrounding an internal cavity of said cage body, at least one thread provided on said outer surface and a plurality of apertures extending through said outer surface, said cage body including a leading end having a first diameter and a trailing end having a second diameter that is larger than said first diameter, wherein said apertures increase in size from said leading end toward said trailing end of said cage body;
   positioning said leading end of said cage body adjacent an intervertebral disc space between an upper vertebral body and a lower vertebral body, wherein said upper and lower vertebral bodies have opposing end faces that define upper and lower limits of said intervertebral disc space;
   while urging said leading end of said cage body into said intervertebral disc space, turning said cage body so that said at least one thread bites into said opposing end faces of said upper and lower vertebral bodies for anchoring said cage body to said upper and lower vertebral bodies.

15. The method as claimed in claim 14, further comprising fully inserting said cage body between said opposing end faces of said upper and lower vertebral bodies so that spacing between said opposing end faces at said trailing end of said cage body is greater than spacing between said opposing end faces at said leading end of said cage body.

16. The method as claimed in claim 14, wherein said opposing end faces of said upper and lower vertebral bodies have first ends and second ends, and wherein said urging step causes greater distraction at said first ends of said opposing end faces than at said second ends of said opposing end faces.

17. The method as claimed in claim 14, further comprising providing a bone-growth inducing material in said internal cavity of said cage body.

18. The method as claimed in claim 17, wherein said trailing end of said cage body includes an opening in communication with said internal cavity of said cage body for providing said bone-growth inducing material in said internal cavity of said cage body.

19. The method as claimed in claim 18, further comprising covering said opening with a cap for retaining said bone-growth inducing material in said internal cavity of said cage body.

20. The method as claimed in claim 19, wherein said opening at said proximal end of said cage body includes internal threads and said end cap has external threads adapted for meshing with said internal threads of said opening.

21. The method as claimed in claim 14, wherein said cage body has a longitudinal axis extending between said leading and trailing ends thereof and a transverse axis extending in a direction that is substantially perpendicular to said longitudinal axis, and wherein said plurality of apertures are clustered about said transverse axis.

22. The method as claimed in claim 21, further comprising turning said cage body between said upper and lower vertebral bodies so that said clustered apertures confront said opposing end faces of said upper and lower vertebral bodies.

23. The method as claimed in claim 14, wherein said leading end of said cage body has a rounded nose, and said outer surface of said cage body has at least one flute extending from said leading end toward said trailing end of said cage body.

24. The method as claimed in claim 14, wherein said cage body is devoid of a flange so that said cage body is anchored to said upper and lower vertebral bodies solely by said at least one thread on said outer surface thereof.

25. The method as claimed in claim 14, wherein said cage body is continuously tapered between said leading end and said trailing end of said cage body.

26. The method as claimed in claim 14, wherein said at least one thread is a continuous thread extending between said leading and trailing ends of said cage body.

* * * * *

UNITED STATES PATENT AND TRADEMARK OFFICE
CERTIFICATE OF CORRECTION

PATENT NO. : 7,608,105 B2  Page 1 of 1
APPLICATION NO. : 11/185418
DATED : October 27, 2009
INVENTOR(S) : Pavlov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 483 days.

Signed and Sealed this

Twelfth Day of October, 2010

David J. Kappos
*Director of the United States Patent and Trademark Office*